United States Patent [19]

Essen-Moller

[11] Patent Number: 5,551,425
[45] Date of Patent: Sep. 3, 1996

[54] POTENTIAL DIFFERENCE AND PERFUSION PRESSURE CATHETER

[75] Inventor: Anders Essen-Moller, Stockholm, Sweden

[73] Assignee: Synectics Medical, Inc., Irving, Tex.

[21] Appl. No.: 375,209

[22] Filed: Jan. 18, 1995

Related U.S. Application Data

[63] Continuation of Ser. No. 60,930, May 13, 1993, abandoned.

[51] Int. Cl.$^6$ .................................................. A61B 5/05
[52] U.S. Cl. ............................................................ 128/635
[58] Field of Search ................................... 128/635, 637, 128/642, 645, 656, 658, 691, 692, 748, 8; 607/115, 116, 120, 133; 604/264, 280; 606/45–48; 204/403, 404, 435

[56] References Cited

U.S. PATENT DOCUMENTS

| | | |
|---|---|---|
| 2,162,656 | 6/1939 | Warrington . |
| 2,168,867 | 8/1939 | George . |

(List continued on next page.)

FOREIGN PATENT DOCUMENTS

| | | | |
|---|---|---|---|
| 0073558 | 3/1983 | European Pat. Off. . | |
| 0080680 | 6/1983 | European Pat. Off. . | |
| 0241644 | 10/1987 | European Pat. Off. . | |
| 0242644 | 10/1987 | European Pat. Off. | 204/403 |
| 0356603 | 11/1993 | European Pat. Off. . | |
| 2162656 | 6/1973 | Germany . | |
| 2453630 | 11/1980 | Germany . | |
| 3140265 | 4/1983 | Germany . | |
| 221635 | 5/1985 | Germany . | |
| 3523987 | 1/1987 | Germany . | |
| 7707275 | 1/1979 | Netherlands . | |
| 178028 | 11/1966 | U.S.S.R. . | |
| 272477 | 5/1968 | U.S.S.R. . | |
| 1502004 | 8/1989 | U.S.S.R. . | |

OTHER PUBLICATIONS

"Clinical relevance of ambulatory 24–hour . . . ", Vogten, et al., 1987, pp. 21–31 in Netherlands Journal of Medicine.
"Computerized Axial Manometry of the Esophagus", Bombeck, et al. in Annals of Surgery, vol. 206, No. 4, pp. 465–472, Oct. 1987.
"The laser motility sensor for long–term study of intraesophageal pressure", Schneider et al., in Primary Motility Disorder of the Esophagus, Giuli et al., eds., pp. 64–69 1991.
Kim et al., American Journal of Clinical Pathology, 1990, vol. 94, pp. 187–191, "The Gastric Juice Urea and Ammonia " . . . .
Butcher et al., Digestion, 1992, vol. 53, pp. 142–148, "Use of an Ammonia Electrode for Rapid Quantification of Helicobacterpylori Urease: Its use in the Endoscopy Room and in the ". . . .
The New Yorker, Sep. 20, 1993, T. Monmaney, "Marshall's Hunch".
"Oesophageal multipurpose monitoring probe", Baker et al., Anaesthesia, 1983, vol. 38, pp. 892–897.
Digestive Diseases, Reprint, vol. 8, Suppl. 1, pp. 60–70, 1990.

(List continued on next page.)

Primary Examiner—Angela D. Sykes
Assistant Examiner—Samuel Gilbert
Attorney, Agent, or Firm—Stephen C. Glazier, P.C.

[57] ABSTRACT

A perfusion catheter is designed to be used both as an exploring catheter for measuring potential difference across the gastrointestinal wall and for simultaneous measurement of pressure at the same site. The catheter includes a perfusion lumen into which an Ag/AgCl wire is inserted as an electrode thus avoiding the need of half cells and bridges. By perfusing saline around the wire, the environment is kept constant around the wire, a prerequisite for the electrode. The flow rate of the distal end of the lumen is altered by making the diameter of the outlet different to the diameter of the lumen. The perfused solution is also used to measure pressure.

8 Claims, 1 Drawing Sheet

U.S. PATENT DOCUMENTS

| | | | |
|---|---|---|---|
| 2,857,915 | 10/1958 | Sheridan . | |
| 3,373,735 | 3/1968 | Gallagher . | |
| 3,480,003 | 11/1969 | Crites . | |
| 3,669,095 | 6/1972 | Kobayashi et al. . | |
| 3,690,309 | 9/1972 | Pluzhnikov et al. . | |
| 3,817,241 | 6/1974 | Grausz . | |
| 3,905,889 | 9/1975 | Macur et al. . | |
| 3,923,626 | 12/1975 | Niedrach et al. . | |
| 4,016,866 | 4/1977 | Lawton | 204/403 X |
| 4,063,548 | 12/1977 | Klatt et al. . | |
| 4,073,287 | 2/1978 | Bradley et al. . | |
| 4,119,498 | 10/1978 | Edwall et al. . | |
| 4,176,659 | 12/1979 | Rolfe . | |
| 4,197,852 | 4/1980 | Schindler et al. . | |
| 4,208,588 | 6/1980 | Rudin . | |
| 4,214,593 | 7/1980 | Imbruce et al. . | |
| 4,265,249 | 5/1981 | Schindler et al. . | |
| 4,299,929 | 11/1981 | Sakano et al. . | |
| 4,299,959 | 11/1981 | Jellinek | 204/403 X |
| 4,381,011 | 4/1983 | Somers . | |
| 4,442,841 | 4/1984 | Uehara et al. | 128/635 |
| 4,471,779 | 9/1984 | Antoshkiw et al. . | |
| 4,476,871 | 10/1984 | Hon . | |
| 4,478,222 | 10/1984 | Koning et al. | 128/635 X |
| 4,486,290 | 12/1984 | Cahalan et al. . | |
| 4,487,206 | 12/1984 | Aagard . | |
| 4,503,859 | 3/1985 | Petty et al. . | |
| 4,508,103 | 4/1985 | Calisi | 128/748 X |
| 4,577,640 | 3/1986 | Hofmeister . | |
| 4,593,701 | 6/1986 | Kobayashi et al. . | |
| 4,600,015 | 7/1986 | Evans et al. . | |
| 4,618,929 | 10/1986 | Miller et al. . | |
| 4,631,061 | 12/1986 | Martin . | |
| 4,632,119 | 12/1986 | Reichstein . | |
| 4,642,104 | 2/1987 | Sakamoto et al. . | |
| 4,655,225 | 4/1987 | Dahne et al. . | |
| 4,681,116 | 7/1987 | Settler . | |
| 4,682,596 | 7/1987 | Bales et al. | 606/45 X |
| 4,691,708 | 9/1987 | Kane . | |
| 4,696,672 | 9/1987 | Mochizuki et al. . | |
| 4,700,709 | 10/1987 | Kraig . | |
| 4,703,757 | 11/1987 | Cohen . | |
| 4,705,503 | 11/1987 | Dorman et al. . | |
| 4,729,384 | 3/1988 | Bazenet . | |
| 4,748,113 | 5/1988 | Marshall . | |
| 4,748,562 | 5/1988 | Miller et al. . | |
| 4,757,194 | 7/1988 | Simms . | |
| 4,776,347 | 10/1988 | Matthews . | |
| 4,796,629 | 1/1989 | Grayzel . | |
| 4,803,992 | 2/1989 | Lemelson . | |
| 4,815,471 | 3/1989 | Stobie . | |
| 4,834,101 | 5/1989 | Collison et al. . | |
| 4,850,371 | 7/1989 | Broadhurst et al. . | |
| 4,873,990 | 10/1989 | Holmes et al. . | |
| 4,887,610 | 12/1989 | Mittal . | |
| 4,892,101 | 1/1990 | Cheung et al. . | |
| 4,901,731 | 2/1990 | Millar | 128/748 |
| 4,924,877 | 5/1990 | Brooks . | |
| 4,966,161 | 10/1990 | Wallace et al. . | |
| 4,975,581 | 12/1990 | Robinson et al. . | |
| 4,976,265 | 12/1990 | Falcial et al. . | |
| 4,981,470 | 1/1991 | Bombeck, IV . | |
| 4,986,671 | 1/1991 | Sun et al. . | |
| 4,991,590 | 2/1991 | Shi . | |
| 4,996,161 | 2/1991 | Conners et al. . | |
| 5,005,584 | 4/1991 | Little . | |
| 5,007,427 | 4/1991 | Suzuki et al. . | |
| 5,018,529 | 5/1991 | Tenerz et al. . | |
| 5,022,396 | 6/1991 | Watanabe . | |
| 5,025,786 | 6/1991 | Siegel . | |
| 5,046,497 | 9/1991 | Millar . | |
| 5,047,627 | 9/1991 | Yim et al. . | |
| 5,054,487 | 10/1991 | Clarke . | |
| 5,103,835 | 4/1992 | Yamada et al. . | |
| 5,105,812 | 4/1992 | Corman . | |
| 5,108,364 | 4/1992 | Takezawa et al. . | |
| 5,117,827 | 6/1992 | Stuebe et al. . | |
| 5,119,498 | 6/1992 | McNeill et al. . | |
| 5,151,598 | 9/1992 | Denen . | |
| 5,158,083 | 10/1992 | Sacristan et al. . | |
| 5,184,619 | 2/1993 | Austin . | |
| 5,199,443 | 4/1993 | Maurer et al. . | |
| 5,207,226 | 5/1993 | Bailin et al. . | |
| 5,280,786 | 1/1994 | Wlodarczyk et al. . | |
| 5,291,884 | 3/1994 | Heinemann et al. . | |
| 5,301,673 | 4/1994 | Rabito et al. . | |
| 5,314,804 | 5/1994 | Boguslaski et al. . | |

OTHER PUBLICATIONS

Scarpignato et al., "Simultaneous Measurement and Recording . . . ".

Hojgaard et al., "A New Method for Measurement of the Electrical Potential Difference Across the Stomach Wall", 1991 pp. 847–858.

"Ambulatory Monitoring of Gastric Emptying", Hoeft et al., May 16, 1993, American Assoc. of the Study of Live Diseases.

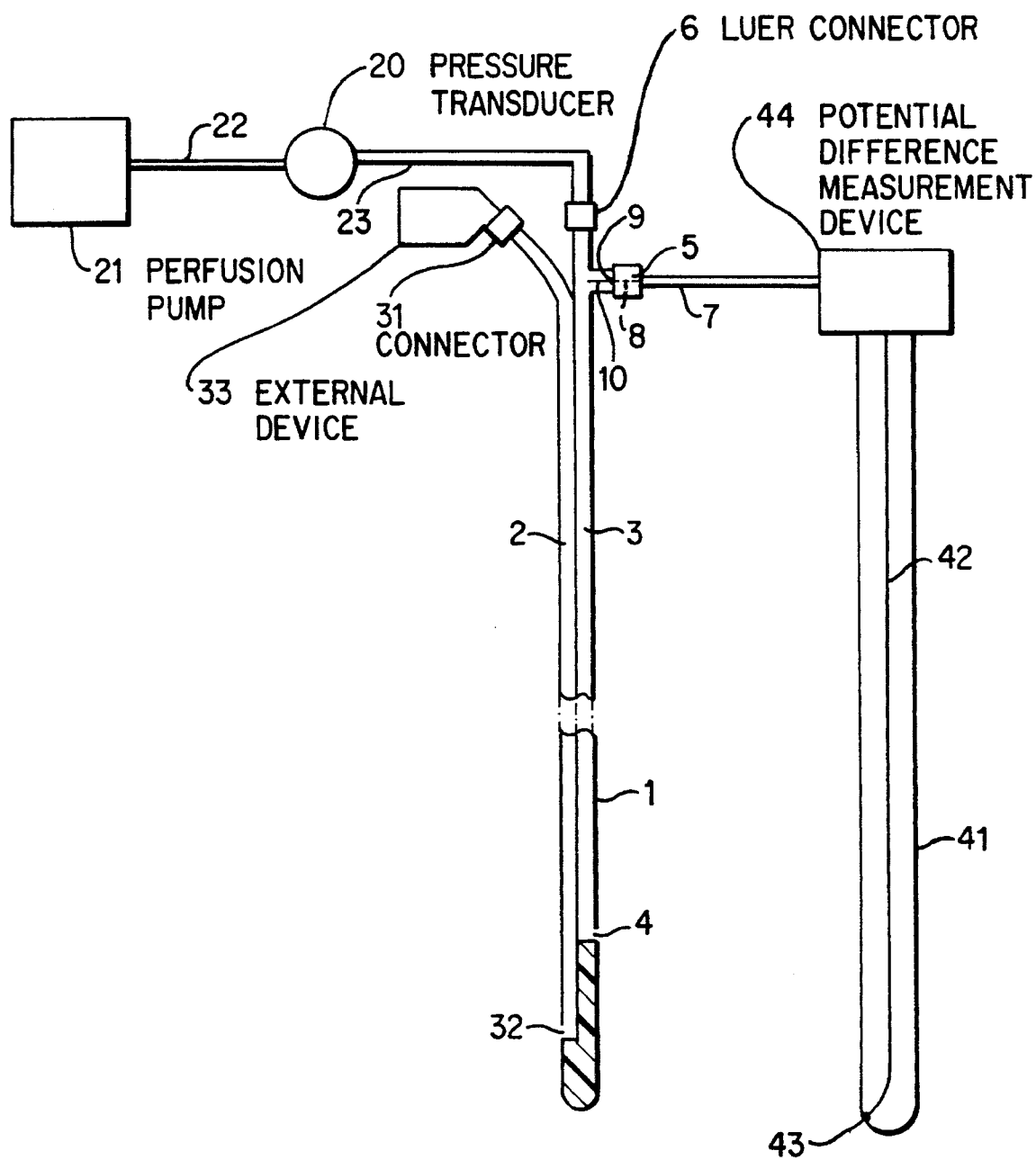

POTENTIAL DIFFERENCE AND PERFUSION PRESSURE CATHETER

This is a continuation of application Ser. No. 08/060,930, filed May 13, 1993, abandoned.

TECHNICAL FIELD

The present invention relates to medical catheters. More particularly the present invention involves a medical catheter with an electrode not involving a half cell or a salt bridge, for use in the gastrointestinal tract simultaneously as (1) an exploring electrode catheter for electrical potential difference measurement across the gastrointestinal mucosa, and (2) for pressure measurement. Both the pressure and electrical potential difference are measured at the same site.

BACKGROUND

Reference electrode catheters for measuring various bodily fluids are well known. These catheters typically include an Ag/AgCl (silver/silver chloride) electrode wire in a compartment filled with a KCl (potassium chloride) solution. The compartment communicates with its outer surroundings by means of a porous plug creating a liquid junction. Said reference electrode catheters can be used as an exploring electrode catheter in potential difference measurement. Other reference electrodes that have been used as exploring electrodes in intragastrointestinal potential difference measurements have included half cells and salt bridges communicating with conducting perfusate in a lumen of a catheter.

Electrical potential difference is the voltage difference between two non-polarizable electrodes on either side of a membrane after elimination of junction potentials (see Hojgard 1991). Because there is little difference in potential between blood in the periphery and the gastrointestinal serosal surface, gastrointestinal transmucosal electrical potential difference is the potential between an intragastrointestinal exploring electrode and an electrically adjacent intravenous reference electrode. An intravenous reference electrode can be an Ag/AgCl reference electrode catheter placed in a saline intravenous infusion line.

A 24 hour pH and potential difference data logger, the Proxima Light, by Synectics Medical, Inc., 1425 Greenway Drive, Suite 600, Irving, Tex. 75038, was described by Scarpignato and Galmiche 1990.

Pressures measured with intragastrointestinal catheters are also well known. Pressure catheters exist where sterile water is perfused by means of a perfusion pump through a lumen in the catheter and out through an opening at the site (often at the distal end of the catheter) where pressure is to be measured. If the pressure changes at said measuring site, a pressure transducer at the proximal end of the catheter will measure the pressure change.

The present invention is a new design for a saline perfused exploring electrode catheter where the exploring Ag/AgCl electrode is directly inserted into the perfusate in a lumen for the measurement of electrical potential difference, while simultaneously using said perfusate for measuring pressure at the same site. The two parameters, potential difference and pressure, are measured simultaneously at the same point and with one measurement lumen only. In this way, two parameters can be measured by the same perfused catheter. In addition, no expensive bridge connection is needed for the exploring electrode.

SUMMARY OF THE INVENTION

The present invention has a simple lumen catheter through which physiological saline solution is perfused. At the proximal end of the catheter a pressure transducer is connected. Also at the proximal end is an Ag/AgCl wire introduction into the lumen for saline perfusion. At the distal end of the catheter is a hole in the catheter through which the saline solution flows out. This hole is of somewhat different diameter than the perfusion lumen itself, which changes the fluid speed at the hole. Normally a perfusion pump is used with steel capillaries to ensure constant flow through the catheter. If the pressure changes at the hole, the pressure transducer will accurately record all of the pressure changes, as long as the pump with its capillary maintains constant flow, and as long as the elasticity and flexing of the perfusion tubing introduces minimal error in the measurements. At the same time the constant flow will provide that the ionic environment is approximately constant around the Ag/AgCl wire, because the diffusion gradient between the catheter filled with saline and the ambient media will remain approximately the same. The different diameter outlet hole provides changed outlet flow speed, and further stabilizes the constant environment around the Ag/AgCl wire. Because the ion chloride concentration of the environment around the Ag/AgCl wire is constant, the wire fulfills the conditions of an exploring electrode for mucosal gastrointestinal potential difference measurement.

The invention uses a second catheter with an electrode at its distal end inserted into a vein, so that the distal ends of the two catheters are electrically adjacent to each other across the gastro-intestinal wall. The electrical potential between the electrode in the first catheter, and the electrode in the second catheter is measured simultaneously with the measurement of the pressure of the perfused saline solution. Electrical potential difference is the voltage difference between the electrodes on either side of the gastro-intestinal wall. Because there is little difference in potential between blood in the periphery and the gastrointestinal serosal surface, gastrointestinal transmucosal electrical potential difference is the potential between an intragastrointestinal electrode and an electrically adjacent intravenous electrode.

BRIEF DESCRIPTION OF THE DRAWING

The FIGURE is a schematic side view of an embodiment of the device of the invention. A one lumen perfusion catheter is shown that can be used for both pressure and potential difference measurement. Also shown is a perfusion pressure transducer and a reference lead.

DETAILED DESCRIPTION OF THE DRAWING

The FIGURE displays a polyurethane perfusion catheter 1 with lumens 2 and 3 where lumen 3 has a distal opening 4 with a diameter slightly smaller (or alternatively, slightly larger) than the diameter in lumen 3, thus changing the flow speed at opening 4 of any liquid that is passed through lumen 3. At the proximal end of lumen 3 are two luer connections 5 and 6. Via a pressure transducer 20, connection 6 is connected by tube 23 to a perfusion pump 21 with a steel capillary 22 which creates a constant flow of perfused solution through said pressure transducer 20 and catheter lumen 3.

Through luer connection 5, a shielded cable 7 is introduced and its wire 8 is soldered at soldering point 9 to an Ag/AgCl wire 10 which is protruding into lumen 3. Soldering point 9 is covered in glue to prevent contact with moisture.

The FIGURE also shows the reference lead (also called herein, the second catheter) 41, with an electrode 43 at its distal end. In this embodiment shown, the electrode 43 communicates with a potential difference measurement device 44 by a wire 42 running inside the second catheter 41. The second catheter 41 with the electrode 43 at is distal end is inserted into a vein, so that the distal ends of the two catheters 1 and 41 are electrically adjacent to each other across the gastrointestinal wall.

The embodiments illustrated and discussed herein are intended only to teach those skilled in the art the best way known by the inventor to make and use the invention. Nothing in the specification should be considered as limiting the scope of the present invention. Changes could be made by those skilled in the art to produce equivalent devices without departing from the invention. The present invention should only be limited by the following claims and their legal equivalents.

For example, the catheter may include other lumens for other or similar purposes than the described lumen 3 without deviating from the present innovation. As an illustration, also shown in the FIGURE is a lumen 2 with proximal connector 31, and distal opening 32. This lumen can be used for other related catheter purposes, simultaneously or sequentially with lumen 3. However, the invention can be practiced without lumen 2, connection 31, and distal opening 32.

I claim:

1. A gastrointestinal catheter device comprising:
   (a) a first catheter having a tubular body with a proximal end, a distal end, an interior, a length, an exterior, and a first lumen running through the interior of the tubular body for the length of the tubular body, the first lumen having a proximal end and a diameter,
   (b) a wire electrode within the first lumen near the proximal end of the tubular body,
   (c) a first outlet at the distal end of the tubular body, communicating from the first lumen to the exterior of the tubular body,
   (d) a first luer connector, at the proximal end of the first lumen, connectable to a pressure transducer,
   (e) an external shielded cable,
   (f) a center wire in said external shielded cable,
   (g) a second luer connector, adjacent to the proximal end of the first lumen, connecting the wire electrode to said external shielded cable,
   (h) a pressure transducer,
   (i) a perfusion pump,
   (j) a tube connecting the first luer connector to the pressure transducer,
   (k) a capillary connecting the pressure transducer to the perfusion pump,
   (l) a second catheter, with a distal end, a proximal end, and an electrode at its distal end, and with a potential difference between the electrode at the distal end of the second catheter and the wire electrode within the first lumen running through the interior of the tubular body of the first catheter, and
   (m) a potential difference measurement device connected to the proximal end of the second catheter and the external shielded cable, the potential difference measurement device electrically communicating with the electrode at the distal end of the second catheter and the wire electrode within the first lumen running through the interior of the tubular body of the first catheter.

2. The invention in claim 1, wherein the wire electrode comprises an Ag/AgCl wire.

3. The invention in claim 2, wherein
   (a) the center wire in the external shielded cable is connected to and penetrates through the second luer connector,
   (b) said center wire in the external shielded cable is soldered to said wire electrode at a solder point and said solder point is covered with glue,
   (c) said wire electrode and said external shielded cable are formed as one integral part and are connectable to the second luer connector, and
   (d) the second luer connector is connected to said first lumen and said wire electrode protrudes into the first lumen.

4. The invention in claim 1, wherein the center wire in the external shielded cable is connected to and penetrates through the second luer connector.

5. The invention in claim 1, wherein the first outlet at the distal end of the tubular body is of a different diameter than the diameter of the first lumen.

6. The invention in claim 1, and further comprising:
   (a) an external device,
   (b) a second lumen in the interior of the tubular body, running through the length of the tubular body, and having a proximal end and a distal end,
   (c) a third luer connector, adjacent to the proximal end of the second lumen, connecting the second lumen to the external device, and
   (d) a second outlet, at the distal end of the second lumen, from the second lumen to the exterior of the tubular body.

7. A gastrointestinal catheter comprising:
   (a) a first catheter having a tubular body with a proximal end, a distal end, an interior, a length, an exterior, and a first lumen running through the interior of the tubular body for the length of the tubular body, the first lumen having a proximal end and a diameter,
   (b) a wire electrode within the first lumen near the proximal end of the body,
   (c) a first outlet at the distal end of the tubular body, communicating from the first lumen to the exterior of the tubular body,
   (d) a first luer connector, at the proximal end of the first lumen, connectable to a pressure transducer,
   (e) an external shielded cable,
   (f) a center wire in said external shielded cable,
   (g) a second luer connector, adjacent to the proximal end of the first lumen, connecting the wire electrode with said external shielded cable,
   (h) a pressure transducer,
   (i) a perfusion pump,
   (j) a tube connecting the first luer connector to the pressure transducer,
   (k) a capillary connecting the pressure transducer to the perfusion pump,
   (l) an external device,
   (m) a second lumen in the interior of the tubular body, running through the length of the tubular body, and having a proximal end and a distal end, (n) a third luer connector, adjacent to the proximal end of the second lumen, connecting the second lumen to the external device, (o) a second outlet, at the distal end of the second lumen, from the second lumen to the exterior of the tubular body, (p) a second catheter, with a distal end, a proximal end, and an electrode at its distal end, and with a potential difference between the electrode at the distal end of the second catheter and the wire electrode within the first lumen running through the interior of the tubular body of the first catheter, and (q) a potential difference measurement device connected to the proximal end of the second catheter and the external shielded cable, the potential difference measurement device electrically communicating with the electrode at the distal end of the second catheter and the wire electrode within the first lumen running through the interior of the tubular body of the first catheter.

8. A method for simultaneously measuring gastrointestinal electrical potential difference and pressure, at one site, comprising the steps of:

(a) inserting a first catheter, having a distal end and a proximal end, into a gastrointestinal area, (b) inserting a second catheter having a distal end and an electrode at the distal end of the second catheter into a vein, so that the distal ends of the first and second catheters are electrically adjacent to each other across a gastro-intestinal wall, (c) perfusing physiological saline solution through a lumen in the first catheter from an exterior of a patient into the proximal end of the first catheter, and out an outlet at the distal end of the first catheter, with an electrode near the distal end of the first catheter inserted into the physiological saline solution in the lumen, (d) measuring an electrical potential between the electrode near the distal end of the first catheter and the electrode at the distal end of the second catheter, and (e) simultaneously measuring pressure of the perfused saline solution.

* * * * *